US010080631B2

(12) United States Patent
Love

(10) Patent No.: US 10,080,631 B2
(45) Date of Patent: Sep. 25, 2018

(54) DENTAL PIPETTE

(71) Applicant: Gail Love, Tacoma, WA (US)

(72) Inventor: Gail Love, Tacoma, WA (US)

( * ) Notice: Subject to any disclaimer, the term of this patent is extended or adjusted under 35 U.S.C. 154(b) by 0 days.

(21) Appl. No.: 15/484,840

(22) Filed: Apr. 11, 2017

(65) Prior Publication Data

US 2018/0098830 A1    Apr. 12, 2018

Related U.S. Application Data

(60) Provisional application No. 62/406,054, filed on Oct. 10, 2016.

(51) Int. Cl.
*A61C 1/10* (2006.01)
*A61C 17/02* (2006.01)
*A61C 3/00* (2006.01)
*A61C 19/06* (2006.01)
*A61M 25/00* (2006.01)
*A46B 11/00* (2006.01)
*A61C 15/00* (2006.01)

(52) U.S. Cl.
CPC ...... *A61C 17/0202* (2013.01); *A46B 11/0041* (2013.01); *A61C 3/005* (2013.01); *A61C 19/063* (2013.01); *A61M 25/007* (2013.01); *A46B 2200/108* (2013.01); *A61C 15/00* (2013.01)

(58) Field of Classification Search
CPC ... A61C 17/0202; A61C 3/005; A61C 19/063; A61J 1/067; A46B 11/0041; A46B 2200/108; A61M 25/007
USPC ......................................................... 433/80
See application file for complete search history.

(56) References Cited

U.S. PATENT DOCUMENTS

| | | | | |
|---|---|---|---|---|
| 1,676,601 A | * | 7/1928 | Cavanaugh | A46B 11/0041 222/212 |
| 2,097,010 A | * | 10/1937 | Arnegger | A46B 11/0041 401/183 |
| 2,640,215 A | * | 6/1953 | Borsini | A46B 11/0041 15/188 |
| 3,292,644 A | * | 12/1966 | Ericson | A46B 11/0041 401/132 |
| 4,049,354 A | * | 9/1977 | O'Rourke | A46B 11/0041 401/134 |
| 4,828,420 A | * | 5/1989 | Otsuka | A46B 7/04 132/329 |
| 4,863,380 A | * | 9/1989 | Creed | A61C 17/0202 132/322 |

(Continued)

*Primary Examiner* — Nicholas Lucchesi
(74) *Attorney, Agent, or Firm* — Global Intellectual Property Agency, LLC; Jordan Sworen

(57) ABSTRACT

A dental pipette. The dental pipette includes a container having a chamber configured to receive and retain fluids therein. A nozzle positioned at one end of the container is in fluid communication with the chamber via a conduit. A plurality of apertures disposed on the nozzle enable fluids within the chamber to be dispensed from the nozzle. A plurality of bristles extend radially outwardly from the nozzle and taper in length from one end of the nozzle to a second end of the nozzle forming a cone-like construction. The apertures and bristles are positioned at intervals and assist with the cleaning of teeth, gums, and the like. A hollow, beveled tip disposed at one end of the nozzle facilitates easy insertion under the gum line and in between teeth. Usage of the dental pipette provides protection from gum infection, bone loss, and tooth loss.

6 Claims, 2 Drawing Sheets

(56) References Cited

U.S. PATENT DOCUMENTS

| | | | | |
|---|---|---|---|---|
| 4,958,751 A * | 9/1990 | Curtis | A61C 19/06 | 222/192 |
| 5,098,291 A * | 3/1992 | Curtis | A46B 11/0017 | 222/402.13 |
| 5,123,841 A * | 6/1992 | Millner | A61C 15/00 | 132/322 |
| 5,238,649 A * | 8/1993 | Nason | A61B 10/02 | 422/411 |
| 5,345,981 A * | 9/1994 | Pavenick | A45D 34/045 | 141/20.5 |
| 5,459,898 A * | 10/1995 | Bacolot | A46B 5/0016 | 15/106 |
| 5,570,966 A * | 11/1996 | Phelan | A46B 11/0041 | 401/183 |
| 6,059,570 A * | 5/2000 | Dragan | A61C 3/005 | 401/129 |
| 6,334,774 B1 * | 1/2002 | Mark | B05C 17/00593 | 401/265 |
| 6,343,717 B1 | 2/2002 | Zhang et al. | | |
| 6,418,940 B1 * | 7/2002 | Tcherny | A61C 15/00 | 132/321 |
| 6,669,475 B2 * | 12/2003 | Kandelman | A46B 7/04 | 132/322 |
| 6,969,210 B1 * | 11/2005 | Newell | A45D 34/04 | 401/284 |
| 8,100,597 B2 | 1/2012 | Sogaro | | |
| 8,657,518 B2 * | 2/2014 | Han | A46B 5/0095 | 15/167.1 |
| 9,402,700 B2 * | 8/2016 | Patel | A61C 15/00 | |
| 2005/0032019 A1 * | 2/2005 | Han | A46B 3/18 | 433/80 |
| 2005/0257338 A1 * | 11/2005 | Brandli | A46B 9/021 | 15/106 |
| 2007/0108235 A1 * | 5/2007 | Sogaro | A61J 1/067 | 222/209 |
| 2007/0148042 A1 | 6/2007 | Ootani et al. | | |
| 2011/0243812 A1 | 10/2011 | Sogaro | | |
| 2012/0318288 A1 * | 12/2012 | Massimi | A46B 11/0041 | 132/200 |
| 2014/0109927 A1 * | 4/2014 | Simard | A46B 9/021 | 132/200 |
| 2015/0033482 A1 * | 2/2015 | Miles | A46B 11/0041 | 15/104.94 |
| 2016/0339206 A1 * | 11/2016 | Cunningham | A61M 25/0041 | |
| 2017/0007002 A1 * | 1/2017 | Langdon | A45D 34/045 | |
| 2017/0172289 A1 * | 6/2017 | Habibi-Naini | A46B 9/028 | |
| 2017/0224097 A1 * | 8/2017 | Reichmuth | A46B 9/026 | |

* cited by examiner

DENTAL PIPETTE

CROSS REFERENCE TO RELATED APPLICATION

This application claims the benefit of U.S. Provisional Application No. 62/406,054 filed on Oct. 10, 2016. The above identified patent application is herein incorporated by reference in its entirety to provide continuity of disclosure.

BACKGROUND OF THE INVENTION

Field of the Invention

The present invention relates to a dental pipette. More specifically, the present invention provides a dental pipette having a chamber configured to store fluid, wherein the fluid is selectively dispensed though a nozzle having a plurality of apertures. The nozzle further includes a plurality of bristles that extend radially outwardly, and taper in a cone-like shape. In this way, the dental pipette may be utilized in the cleaning of teeth or used in other oral applications.

Proper oral hygiene is essential to maintain a healthy lifestyle. Brushing and other oral maintenance, such as disturbing bacterial plaque on a regular basis, prevents periodontal disease and tooth decay from occurring. The absence of proper oral hygiene may result in gum infection, bone loss, and tooth loss.

Devices have been disclosed in the known art that relate to dental hygiene. These include devices that have been patented and published in patent application publications. These devices in the known art have several known drawbacks.

Unfortunately, neither tooth brushing nor flossing can reach into many areas of the mouth, especially bone loss areas. Nor can they dispense antibacterial products such as undiluted antibacterial oral rinses. Some other devises, such as water flossers, can only be used with relatively large amounts of water and thereby diluted rinses. Other devices contain metal or hard plastic tips which can cause pain when contacting exposed root surfaces.

In light of the devices disclosed in the known art, it is submitted that the present invention substantially diverges in design elements from the devices in the known art and consequently it is clear that there is a need in the art for an improvement to existing dental pipette devices. In this regard the instant invention substantially fulfills these needs.

SUMMARY OF THE INVENTION

In view of the foregoing disadvantages inherent in the known types of dental pipettes now present in the art, the present invention provides a new dental pipette wherein the same can be utilized for providing convenience for the user when cleaning one's mouth or another's mouth.

It is therefore an object of the present invention to provide a new and improved dental pipette having a chamber configured to store fluid, wherein the fluid is selectively dispensed though a nozzle by squeezing the container.

It is another object of the present invention to provide a dental pipette, wherein the nozzle includes a plurality of bristles that extend radially outwardly, and taper in length, thereby allowing difficult to reach areas of the mouth to be cleaned by irrigation and brushing.

Another object of the present invention is to provide a dental pipette with a nozzle having a beveled and flexible tip for insertion under a gum line and in between the teeth.

Another object of the present invention is to provide a dental pipette that may be readily fabricated from materials that permit relative economy and are commensurate with durability.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
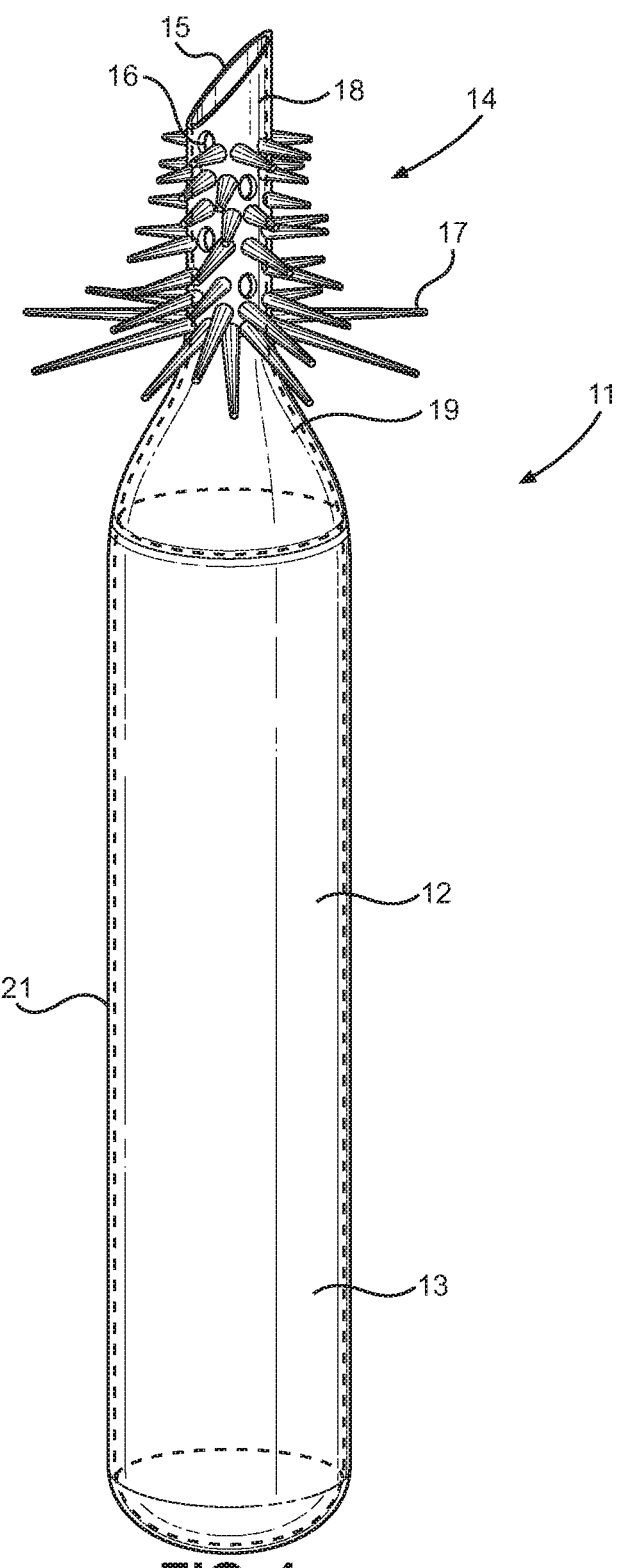
FIG. 1 shows a perspective view of the dental pipette.

Reference is made herein to the attached drawings. Like reference numerals are used throughout the drawings to depict like or similar elements of the dental pipette. For the purposes of presenting a brief and clear description of the present invention, the preferred embodiment will be discussed as used for cleaning of the oral cavity. The figures are intended for representative purposes only and should not be considered to be limiting in any respect.

Referring to FIG. 1, there is shown a perspective view of the dental pipette. The dental pipette 11 provides a pocket storable tooth and mouth cleaning device that enables users to effectively disturb and flush away plaque and food debris. The dental pipette 11 comprises a container 12 having a chamber 13 that is in fluid communication with a nozzle 14. The nozzle 14 is disposed at a first end 19 of the container 12, and includes a conduit 18 that allows the flow of fluid therethrough. The nozzle 14 extends outwardly from the first end 19 and includes a length and width less than the length and width of the container 12. In the shown embodiment, the nozzle 14 includes a plurality of apertures 16 positioned longitudinally along its linear length, wherein each of the apertures 16 are adapted to dispense fluid from the chamber 13. A tip 15 is configured for easy insertion under the gum line and in between teeth, wherein the tip 15 is in fluid communication with the chamber 13.

In the shown embodiment, the container 12 is generally cylindrical. The chamber 13 is configured to store fluid therein, and has a volume of between zero and 0.5 cubic inches. Further, the container 12 includes a flexible sidewall 21 configured to dispense a fluid content of the chamber 13 through the plurality of apertures 16 when squeezed together. Further, the flexible sidewall 21 is biased to return to a squeezed position. Thus, the chamber 13 may be filled with fluid by selectively squeezing the container 12, thereby decreasing the interior volume of the chamber 13, submerging the apertures 16 in a fluid, such as cleaning solution, and releasing the sidewalls 21 to cause a relative pressure difference that fills the chamber 13 with fluid.

In the shown embodiment, a plurality of bristles 17 extending radially outwardly from the nozzle 14, wherein the plurality of bristles 17 taper in length from a first end of the nozzle 14 to a second end of the nozzle 14, thereby forming a cone-like structure.

Figure 2:
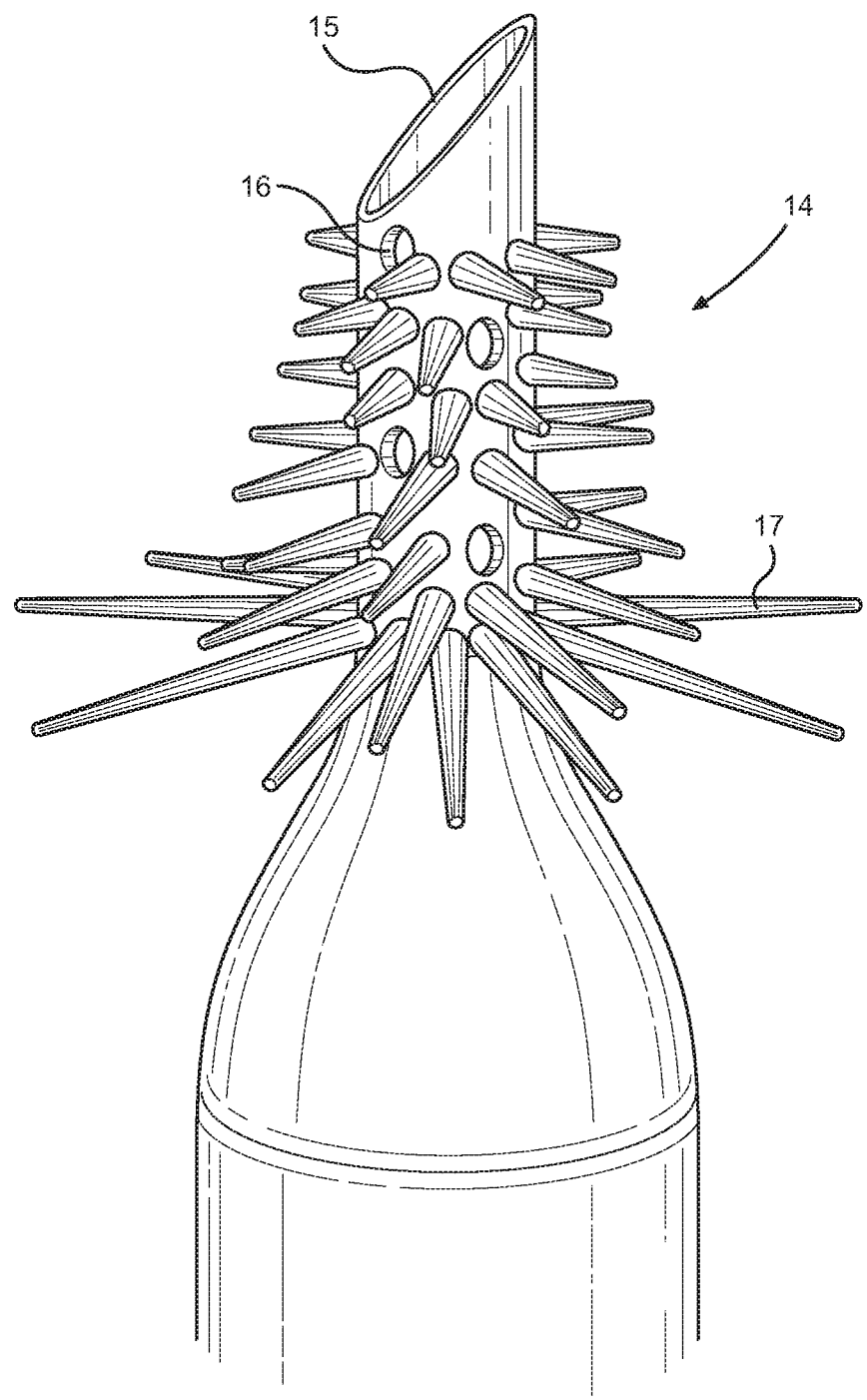
FIG. 2 shows a close-up view of the nozzle of the dental pipette.

Referring to FIG. 2, there is shown a close up of the nozzle of the dental pipette. In the shown embodiment, the nozzle 14 includes a hollow tip 15. The hollow tip 15 includes an elongated, flexible beveled tip for easy insertion under the gum line and in between teeth. In the depicted embodiment, the plurality of bristles 17 are soft silicone, conically shaped bristles that are disposed annularly around the nozzle 14. The bristles 17 bristles taper in size from a larger bristle length to a lesser bristle length towards the slightly elongated flexible beveled tip 15 such that they are arranged in a cone-like shape around the nozzle 14. In another embodiment, the plurality of bristles 17 are tapered in a different configuration. In yet another embodiment, the bristles 17 are disposed only on one portion or hemisphere of the nozzle 14.

In one embodiment, each of the plurality of apertures 16 have a diameter of between five millimeters and zero millimeters. However, in alternative embodiments, the diameter of the apertures 16 may vary individually and independent of each other. Further, the apertures 16 are arranged in a staggered configuration along the length of the nozzle 14, thereby discharging fluid generally equally therearound. However, in other embodiments, the apertures 16 are not in a staggered configuration, rather are distributed in uniform rows and columns. Alternatively, the apertures 16 may have any other dimension or configuration. In this way, the plurality of apertures 16 are oriented at various angles thereabout the nozzle 14 thereby providing fluid to be dispensed at various angles therefrom. For example, adjacent apertures 16 may be angled approximately twenty degrees from each other, when measured from a longitudinal axis positioned through a center of the nozzle 14.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A dental pipette, comprising:
   a container including a chamber in fluid communication via a conduit with a nozzle disposed at a first end, the chamber configured to store fluid therein;
   the container having a tapered neck connecting to a first end of the nozzle, the nozzle being un-tapered and forming an open, hollow, and beveled tip at a distal second end thereof;
   the nozzle including a plurality of apertures positioned at intervals therealong, each aperture extending directly through a sidewall of the nozzle;
   a plurality of bristles extending radially outwardly from the nozzle, wherein the plurality of bristles taper in length from a maximum diameter at the first end of the nozzle to a minimum diameter at the distal second end of the nozzle wherein a first side of the beveled tip forms towards the distal second end of the nozzle and adjacent a distalmost bristle of the plurality of bristles, the plurality of bristles forming a cone-like structure around the nozzle;
   wherein an entire region of the plurality of apertures overlaps with an entire region of the plurality of bristles;
   the plurality of apertures disposed annularly about a perimeter of the nozzle.

2. The dental pipette of claim 1, wherein:
   the container and the nozzle are of unitary construction.

3. The dental pipette of claim 1, wherein:
   the container comprises a flexible sidewall, the flexible sidewall configured to dispense a fluid content of the chamber through both the plurality of apertures and the hollow tip when squeezed radially inwardly.

4. The dental pipette of claim 3, wherein:
   the flexible sidewall is biased to return to a non-squeezed position.

5. The dental pipette of claim 1, wherein:
   each of the plurality of apertures comprise a diameter less than or equal to 5 mm.

6. The dental pipette of claim 1, wherein:
   the nozzle includes a length and a width less than a length and a width of the container.

* * * * *